United States Patent
Unger

Patent Number: 5,976,500
Date of Patent: Nov. 2, 1999

[54] GEL PARTICLE CONTRAST MEDIA FOR MAGNETIC RESONANCE IMAGING

[75] Inventor: Evan C. Unger, Tucson, Ariz.

[73] Assignee: ImaRx Pharmaceutical Corp., Tucson, Ariz.

[21] Appl. No.: 08/285,977

[22] Filed: Aug. 4, 1994

Related U.S. Application Data

[62] Division of application No. 08/062,325, May 14, 1993, Pat. No. 5,358,702, which is a continuation of application No. 07/794,437, Nov. 19, 1991, abandoned, which is a continuation-in-part of application No. 07/507,125, Apr. 10, 1990, abandoned.

[51] Int. Cl.$^6$ .................................................. A61B 5/055
[52] U.S. Cl. ........................... 424/9.32; 424/9.36; 514/6; 514/54; 514/57; 514/59; 514/60; 514/836; 600/420
[58] Field of Search ................. 424/9.32, 9.36; 436/173, 806; 514/54, 57, 59, 60, 6, 836; 128/653.4, 654; 600/420

[56] References Cited

U.S. PATENT DOCUMENTS

| | | | |
|---|---|---|---|
| 4,024,073 | 5/1977 | Shimizu et al. | 252/316 |
| 4,101,435 | 7/1978 | Hasegawa et al. | 252/62.53 |
| 4,225,592 | 9/1980 | Lakatos et al. | 424/180 |
| 4,452,773 | 6/1984 | Molday | 424/1.1 |
| 4,501,726 | 2/1985 | Schröder | 424/1.1 |
| 4,692,325 | 9/1987 | Kritzler | 424/4 |
| 4,735,796 | 4/1988 | Gordon | 424/9 |
| 4,749,560 | 6/1988 | Elgavish | 424/9 |
| 4,822,594 | 4/1989 | Gibby | 424/9 |
| 4,849,210 | 7/1989 | Widder | 424/9 |
| 4,863,715 | 9/1989 | Jacobsen et al. | 424/9 |
| 4,965,007 | 10/1990 | Yudelson | 252/62.53 |
| 4,985,233 | 1/1991 | Klaveness | 424/9 |
| 4,986,980 | 1/1991 | Jacobsen | 424/9 |
| 5,043,101 | 8/1991 | Gordon | 252/408.1 |
| 5,114,703 | 5/1992 | Wolf et al. | 425/5 |
| 5,128,121 | 7/1992 | Berg et al. | 424/9 |
| 5,160,725 | 11/1992 | Pilgrimm | 424/9 |

FOREIGN PATENT DOCUMENTS

WO 83/03920  11/1983  WIPO.

OTHER PUBLICATIONS

Atkins and Nieduszynski, "Structural Components of Alginic Acid. II. The Crystalline Structure of Poly-α-$_L$-Guluronic Acid. Results of X-Ray Diffraction and Polarized Infrared Studies", *Biopolymers 12:* 1879–1887 (1973).

Brown, R.E., *Ultrasonography: Basic Principles and Clinical Applications,* Ch. 1 "Basic Principles", pp. 3–22 (Warren H. Green, Inc., St. Louis, MO 1975).

Grant et al, "Biological Interactions Between Polysaccharides and Divalent Cations: The Egg–Box Model", *Febs Letters 32:* 195–198 (1973).

Kean, D.M. and Smith, M.A., Magnetic Resonance Imaging: Principles and Applications (William and Wilkins, Baltimore 1986).

Kennedy et al., "Synthesis of Metal–Complexing Polymers. I. Phosphorylated Polymers", *J. App. Chem.* 8: 459–464 (1958).

Lee, J.K.T., Sagel, S.S. and Stanley, R.J., eds. *Computed Body Tomography,* Ch. 1 "Physical Principles and Instrumentation" by Michel M. Ter–Pogossian pp. 1–7 (Raven Press, New York 1933).

Leonard et al., "A New Synthetic Elastomer Based on a Chlorophosphonated Polyolefin. II. Effect of Polyolefin Structure on Vulcanizate Properties", *J. App. Polymer Sci.* 55: 799–810 (1961).

(List continued on next page.)

*Primary Examiner*—Gary E. Hollinden
*Attorney, Agent, or Firm*—Woodcock Washburn Kurtz Mackiewicz & Norris LLP

[57] ABSTRACT

A contrast medium useful for diagnostic imaging is provided. The contrast medium comprises gel particles, preferably of less than about 90μ in mean diameter, the gel particles comprising at least one polymer entrapping at least one contrast enhancing metal.

36 Claims, 1 Drawing Sheet

OTHER PUBLICATIONS

Lomant and Fairbanks, "Chemical Probes of Extended Biological Structures: Synthesis and Properties of the Cleavable Protein Cross–linking Reagent [$^{35}$S] Dithiobis(succinimidyl propionate)", *J. Mol. Biol. 104:* 243–261 (1976).

Marvel et al., "Vinyl–Type Polymers Containing Phosphorus", *J. of Polymer Sci. 8:* 495–502 (1952).

Odian, *Principles of Polymerization* McGraw–Hill Co., NY, NY pp. 1–39, 96–113 and 611–615 (1970).

Pilgrimm, "Stabilized Suspension of Magnetic Particles and Its Preparation and Use in NMR Diagnosis", *Chemical Abstracts 112:* 380 No. 51778y (1990).

Remington's Pharmaceutical Sciences, Gennaro, A.R., ed., Mack Publishing Company, Easton, PA (1985).

Sander et al., "Phosphorylation of Polymers", *J. Macromol. Sci., Rev, Macromol. Chem.*, vol. 2 57–62 (1968).

Schroeder and Sopchak, "The Reaction of Phosphorus Trichloride and Oxygen with Polymers", *J. of Polymer Sci 47:* 417–433 (1960).

Squire, L.F., *Fundamentals of Radiology,* 3rd ed., Ch. 1 "Introduction and Basic Concepts", pp. 1–11 (Harvard University Press, Cambridge, MA 1982).

Staros, "N–Hydroxysulfosuccinimide Active Esters: Bis(N–hydroxysulfosuccinimide) Esters of Two Dicarboxylic Acids Are Hydrophilic, Membrane–Impermeant, Protein Cross–Linkers", *Biochemistry 21:* 3950–3955 (1982).

Vollmert, *Polymer Chemistry* Springer–Verlag, NY, NY pp. 1–8, 541–561 (1973).

The United States Pharmacopeia—The National Formulary, Jan. 1, 1990, Mack Printing Company, Easton, PA pp. 1857–1859.

GEL PARTICLE CONTRAST MEDIA FOR MAGNETIC RESONANCE IMAGING

REFERENCE TO RELATED APPLICATIONS

This is a divisional of application Ser. No. 062,325, filed May 14, 1993, now U.S. Pat. No. 5,358,702, which in turn is a continuation of application Ser. No. 794,437, filed Nov. 19, 1991, now abandoned which in turn is a continuation-in-part of application Ser. No. 507,125, filed Apr. 10, 1990, now abandoned.

BACKGROUND OF THE INVENTION

Field of the Invention

There are a variety of imaging techniques that have been used to diagnose disease in humans. One of the first imaging techniques employed was X-rays. In X-rays, the images produced of the patients' body reflect the different densities of body structure. To improve the diagnostic utility of this imaging technique, contrast agents are employed to increase the density between various structures, such as between the gastrointestinal tract and its surrounding tissue. Barium and iodinated contrast media, for example, are used extensively for X-ray gastrointestinal studies to visualize the esophagus, stomach, intestines and rectum Ultrasound is another imaging technique In ultrasound, sound is transmitted into a patient via a transducer. When the sound waves propagate through the body, they encounter interfaces from tissues and fluids in the body, and the ultrasound sound waves are either reflected or absorbed. When sound waves are reflected by an interface they are detected by the receiver in the transducer and processed to form an image. The acoustic properties of the tissues and fluids within the body determine the contrast which appears in the resultant image. Contrast agents have been sought which will increase the acoustic difference between the target area and the surrounding area. For example, heavy metals have been tested as contrast agents for ultrasound.

Magnetic resonance imaging (MRI) is a relatively new imaging technique which, unlike X-rays, does not utilize ionizing radiation. As in computed tomography, MRI can make cross-sectional images of the body, however, MRI has the additional advantage of being able to make images in any scan plane (ice, axial, coronal, sagittal or orthogonal). Unfortunately, the full utility of MRI as a diagnostic modality for the body is hampered by the lack of effective contrast agents. Contrast agents have been developed for MRI to improve detection of disease, but most of these efforts have been directed to using chelates of paramagnetic ions as contrast agents. Traditionally employed chelates have the disadvantage of decreasing the relaxivity of the chelate ion as well as potentially causing toxicity, should the metal ion escape from the chelate. Such chelates have the further disadvantage that they are rapidly cleared by the kidneys and do not work as effective contrast agents for imaging of the liver, for example. If better contrast agents were available, the overall usefulness of MRI as an imaging modality would improve.

New and/or better contrast agents for use in X-ray, ultrasound and MRI imaging, and in other imaging systems, are needed. The present invention is directed to these and other important ends.

SUMMARY OF THE INVENTION

The present invention pertains to contrast media useful for diagnostic imaging. Specifically, in one aspect, the present invention is directed to contrast media comprising gel particles, preferably of less than about 90$\mu$ in mean diameter, said gel particles comprising at least one polymer entrapping at least one contrast enhancing metal. Preferably the polymers employed are not cross-linked. The present invention also pertains to contrast media prepared by combining at least one polymer and at least one contrast enhancing metal, optionally in the presence of a gelling agent, to form a gel, and particularizing the mixture to form particles, as well as processes for preparing the same.

The subject invention also pertains to methods for providing an image of an internal region of a patient, said methods comprising (i) administering to the patient one or more of the aforementioned contrast agents, and (ii) scanning the patient using magnetic resonance, ultrasound or X-ray imaging to obtain visible images of the region. In addition, the present invention encompasses a method for diagnosing the presence of diseased tissue in a patient comprising (i) administering to the patient one or more of the foregoing contrast agents, and (ii) scanning the patient using magnetic resonance, ultrasound, or X-ray imaging to obtain visible images of any diseased tissue in the patient.

Further, kits comprising compounds of the present invention and conventional diagnostic kit components are provided.

These and other aspects of the invention will become more apparent from the following detailed description when taken in conjunction with the following drawing.

BRIEF DESCRIPTION OF THE DRAWINGS

FIG. 1 is a schematic representation of a possible structural configuration for the gel particles of the invention. Specifically.

DETAILED DESCRIPTION OF THE INVENTION

Figure 1A:
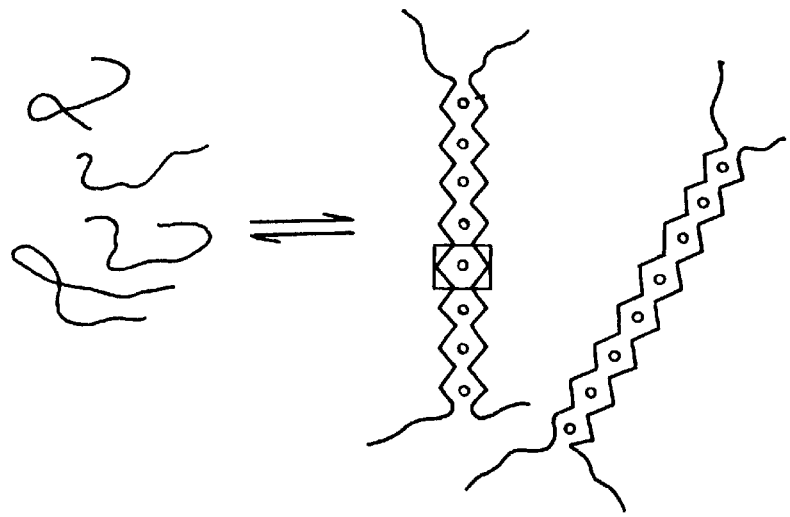
FIG. 1a is a schematic representation showing the association of polymer chains by entrapment of metal ions according an "egg box" model.

Contrast media comprising gel particles having one or more polymers entrapping one or more contrast enhancing metals are provided in the present invention. These contrast media have been shown to be heat stable and stable in long term storage, both of obvious advantage in commercial use. They have also been shown to require a lower overall concentration of contrast enhancing metals, often to achieve the same or better imaging than some other metal-containing contrast media known heretofore By minimizing the amount of metal, toxicity as well as cost may be reduced, since less of the often more expensive and potentially toxic metals are used. Contrast media of the invention have been found to be highly effective contrast agents, useful in many different applications.

Any of a wide variety of biocompatible polymers known in the art may be employed in preparing the media of the present invention. The term biocompatible, used herein in connection with the term polymer, is employed in its conventional sense, that is, to denote polymers that do not substantially interact with the tissues, fluids and other components of the body in an adverse fashion in the particular application of interest. As will be readily apparent to those skilled in the art, there are numerous types of such polymers available. For example, the polymers useful in the present invention can be of natural, synthetic or semisynthetic origin. The term semisynthetic polymer, as employed herein, denotes a natural polymer that has been chemically modified in some fashion. Preferably, the polymer is natural or semisynthetic, most preferably natural. Further, as used herein, the term polymer denotes a compound comprised of two or more repeating monomeric units, preferably three or more repeating monomeric units, more preferably five or more repeating units, and most preferably ten or more repeating units.

Exemplary natural polymers suitable for use in the present invention may include naturally occurring polysaccharides such as, for example, arabinans, fructans, fucans, galactans, galacturonans, glucans, mannans, xylans (such as, for example, inulin), levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xanthin gum, starch, and various other natural homopolymers or heteropolymers such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid; as well as naturally occurring derivatives thereof. Exemplary natural polymers may also include, for example, polypeptides and polyalcohols, as will be readily apparent to those skilled in the art. Exemplary semisynthetic polymers include such modified natural polymers as carboxymethylcellulose, hydroxymethylcellulose, hydroxypropylmethylcellulose, methylcellulose and methoxycellulose. Exemplary synthetic polymers suitable for use in the present invention include polyethylenes (such as, for example, polyethylene glycol, polyoxyethylene, polyoxyethylene glycol, and polyethylene terephthlate), polypropylenes (such as, for example, polypropylene glycol), polyurethanes (such as, for example, polyurethane ureas), pluronic acids and alcohols, polyvinyls (such as, for example, polyvinyl alcohol, polyvinylchloride and polyvinylpyrrolidone), nylon, polystyrene, polylactic acids, fluorinated hydrocarbons, fluorinated carbons (such as, for example, polytetrafluoroethylene), polyacrylates (such as polymethylmethacrylate), polyacrylic acids (such as polymethacrylic acid) and polyacrylamides, as well as derivatives thereof.

Such polymers may range in size, for example, from a molecular weight of about 500 to about 500,000. In some instances, the preferable molecular weight of the polymers is from about 100,000 to about 500,000. To suit other parameters, preferable molecular is from about 500 to about 100,000. Preferably, the polymer employed is one which has a relatively high water binding capacity, that is, a polymer which is capable of binding at least about 50% of its weight in water. When imaging of the gastrointestinal region is desired, preferably the polymer chosen is one which is not substantially absorbed from or degraded within the gastrointestinal region.

Preferred polymers include polygalacturonic acid and pectins. As those skilled in the art are aware, pectins are generally methyl esters of polygalacturonic acid. Particularly preferred are low methoxy pectins. By the phrase "low methoxy", it is meant a pectin having less than about 40% methoxylation (that is, less than about 40% of the carboxylic acid groups are converted to methylesters). As those skilled in the art will recognize, the degree of methoxylation of pectin may be measured by titrating the pectin with base.

Numerous contrast enhancing metals which are suitable for use in the present invention are known to those skilled in the art and include, for example, paramagnetic ions and/or heavy metal ions. Exemplary metals useful, for example, in magnetic resonance imaging include paramagnetic metal ions such as gadolinium, manganese ($Mn^{+2}$ and $Mn^{+3}$), copper, chromium, iron ($Fe^{+2}$ and $Fe^{+3}$), cobalt, erbium, nickel, europium, technetium, indium, samarium, dysprosium, ruthenium, ytterbium, yttrium, and holmium, most preferably manganese ($Mn^{+2}$) Exemplary metals useful, for example, in ultrasound or X-ray imaging are heavy metals such as hafnium, lanthanum, ytterbium, dysprosium and gadolinium. These and other contrast enhancer metals useful in magnetic resonance, ultrasound, and X-ray imaging will be readily apparent to those skilled in the art.

To prepare the contrast media of the present invention, an admixture is first formed between the polymers and the contrast enhancing metals. By admixture it is meant that the contrast enhancing metals are added to the polymer containing medium, and are not chemically bound to the polymer molecules by a covalent linkage. Partial or complete gelation of the polymers to entrap the contrast enhancing metals may occur spontaneously, simply upon adding these two components together. For example, agarose and high methoxy (greater than about 40%) pectin polymers will generally gel spontaneously and entrap the contrast enhancing metals merely upon addition of such metals to the polymers. In other embodiments of the present invention, partial or complete gelation of an admixture may occur as a result of, or be facilitated by, the addition of a gelling agent, thereby causing entrapment of the contrast enhancing metals by the polymers. By "entrap", or variations thereof, as used herein in connection with polymers entrapping contrast enhancing metals, it is meant that the polymers physically surround or enclose the metals. Such entrapment may occur through electrostatic interactions, hydrogen bonding, van der Waals forces, or the like.

Specifically, to cause gelation with polymers and metals which do not spontaneously gel, or to enhance gelation, gelling agents such as polyvalent metal cations, sugars and polyalcohols may be employed. Exemplary polyvalent metal cations useful as gelling agents include calcium, zinc, manganese, iron and magnesium Useful sugars include monosaccharides such as glucose, galactose, fructose, arabinose, allose and altrose, disaccharides such as maltose, sucrose, cellobiose and lactose, and polysaccharides such as starch. Preferably, the sugar is a single sugar, that is, monosaccharide or a disaccharide. Polyalcohol gelling agents useful in the present invention include, for example, glycidol, inositol, mannitol, sorbitol, pentaerythritol, galacitol and polyvinylalcohol. Most preferably, the gelling agent employed in the present invention is sucrose and/or calcium. The particular gelling agents which may be employed in the various formulations of the present invention will be readily apparent to one skilled in the art, once armed with the present disclosure. For example, sucrose is particularly useful for gelling admixtures of polygalacturonic acid and manganese. Similarly, low methoxy pectins gel especially quickly upon addition of calcium ions. It should be noted that some overlap exists between the polymers and contrast enhancing metals, and the gelling agents. Some agents are useful as polymers or contrast enhancing metals, as well as being additionally useful to cause gelation in mixtures of polymers and contrast enhancing metals which do not spontaneously gel. For example, sucrose is a useful polymer molecule, however, it may also be added to an admixture of, for example, polygalacturonic acid and manganese to effect gelation of the admixture. Further, iron may be effective as both a contrast enhancing metal and a gelling agent to cause gelation of an admixture which does not spontaneously gel.

Figure 1B:
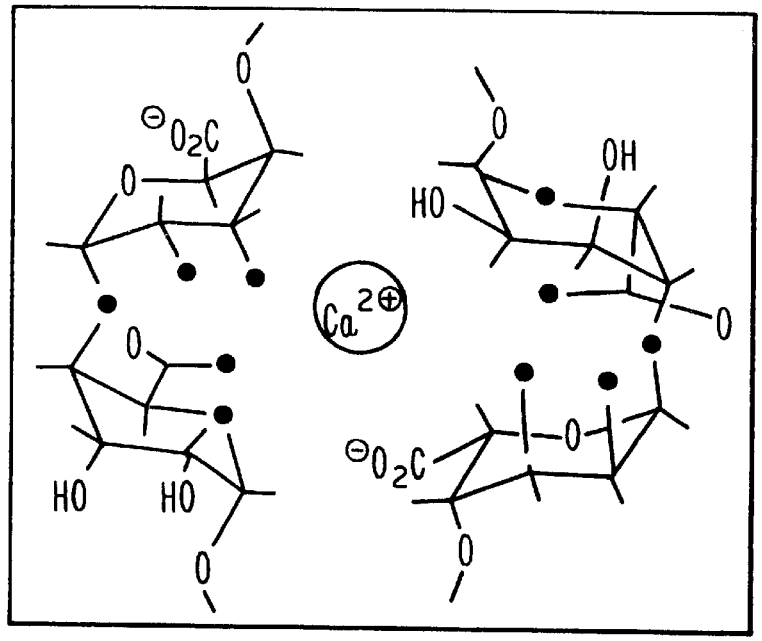
FIG. 1b is a detail of the boxed region of FIG. 1a in which oxygen atoms are shown to coordinate with the divalent cation, $Ca^{+2}$.
Figure 1C:
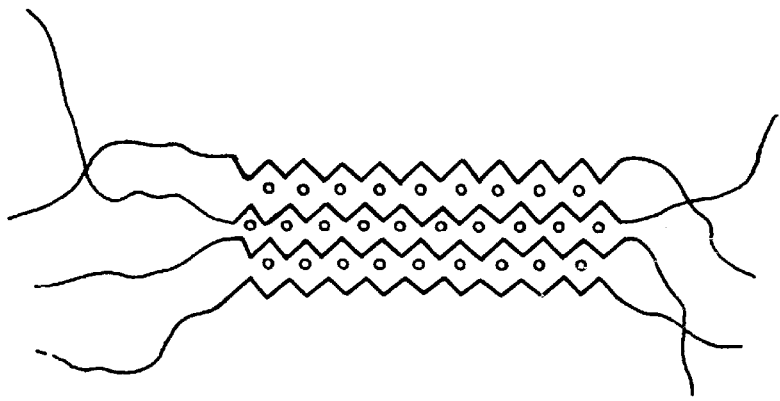
FIG. 1c is a schematic representation of a more complex structural configuration involving stacking of a number of polymer chains.

Although not intending to be bound to any particular theory, it is believed that the polymer molecules and contrast enhancing metals of the present invention arrange during the gelation process in an "egg box" type configuration such as that described in FIG. 1 and in Grant, et al. *FEBS Letters*, Vol. 32, No. 1, pp. 195–198 (1973), or in a tight coil-like aggregation such as that described in Vollmert, *Polymer Chemistry*, pp. 1–8, 541–561, Springer-Verlag, N.Y., New York (1973), the disclosures of each of which are hereby incorporated herein by reference in their entirety. Specifically, in a solution of polymers, the polymers are believed to be in random motion. Upon the addition of a contrast enhancing metal and, in some instances a gelling agent, however, the polymer chains are believed to be brought together by the interaction of the polymers with the contrast enhancing metals and/or gelling agents to "entrap" the contrast enhancing metals, thereby forming "egg boxes" or tight aggregation around the metals. Such phenomenon are discussed, in part, in Atkins, et al., *Biopolymers*, Vol. 12, pp. 1879–1887 (1973), the disclosures of which are hereby incorporated herein by reference in their entirety. In particular, it is believed that the contrast enhancing metals and/or the polyvalent metal cation gelling agents form bridges between two or more adjacent polymers, thereby effecting gelation. It is also believed that the sugars or polyalchohol polymers and/or gelling agents provide a lower energy state, thereby allowing the polymers and contrast enhancing metals to gel more effectively.

As those skilled in the art will recognize, admixtures of polymers, contrast enhancing metals, and optionally gelling agents, will form gels of different consistencies, depending upon the particular formulation employed. For example, calcium ions form relatively firm gels with various polymers, while manganese and ferrous ions form relatively weaker, somewhat watery, gels. In the context of the present invention, the term gel refers to a semisolid material, and includes both watery and firm gels. Preferably, the gel is firm. Firm gels are gels that have lost fluidity, as indicated by the inability of gas bubbles to rise in the gel. This phenomenon is described, for example, in Odian, *Principles of Polymerization*, pp. 1–39, 96–112 and 611–614, McGraw-Hill Co., N.Y. N.Y. (1970), the disclosures of which are hereby incorporated herein by reference in the entirety. For example, a watery gel will generally be formed by a combination of manganese and polygalacturonic acid, whereas a firm gel will generally be formed by a combination of manganese, polygalacturonic acid and calcium. As those skilled in the art would be aware, once armed with the present disclosure, the degree of gel firmness is related to the degree in which the polymer is capable of stably retaining the contrast enhancing metal. Generally, firm gels are capable of retaining at least about 50% of the contrast enhancing metal in prolonged (greater than 24 hours) dialysis against physiological saline, preferably at least about 60% of the contrast enchancing metal, more preferably at least about 70% of the contrast enhancing metal, even more preferably at least about 80% of the contrast enchancing metal, and most preferably at least about 90% of the contrast enhancing metal.

In accordance with the invention, the resultant gel may then be treated to form gel particles. Such treatment may include any one of a variety of techniques, as will be readily apparent to those skilled in the art, such as blenderizing, microemulsification, microfluidization, extrusion, sonication, lyophilization, ball mixing, colloid mixing., etch, as well as any and all combinations thereof. Blenderizing, for example, may be accomplished by using any of a number of commercial blenders, and may be followed, if desired, by extrusion with a commercial extruder device having a filter of a defined size. These and other processes are well known to those skilled in the art. The term particularizing, and variations thereof, as used herein, refers to the formation of small particles, preferably of relatively uniform size, by any of the aforementioned or other processes.

By employing the foregoing methods, gel particles of micrometer or nanometer size may be prepared. Preferably the particles have diameters of less than about $90\mu$, more preferably, diameters ranging from about 5 nm to about $90\mu$. The larger gel particles such as those ranging from about $1\mu$ to about $90\mu$, are particularly useful for parenteral applications, and in gastrointestinal studies. The smaller gel particles such as those ranging in mean diameter from about 5 nm to about 400 nm, more preferably from about 10 nm to about 200 nm, are particularly useful contrast media for intravenous injections, for imaging the liver, and for controlling biodistribution. The terms nanogels and microgels, as used in connection with the present invention, denote gel particles ranging from about 1 nm to less than 1000 nm (less than $1\mu$) (nanogels) and from $1\mu$ (1000 nm) to about $1000\mu$ (microgels).

Gel particles prepared in accordance with the present invention are stable to heat and long term storage, characteristics which make these contrast media especially attractive as a diagnostic agent. The gel particles of the invention may be stored dried, or alternatively may be stored in an aqueous media.

Wide variations in the amounts of polymer, contrast enhancing metal, and gelling agent may be employed in the contrast medium of the present invention. Preferably, however, the polymer is present in a concentration of at least about 1%, by weight, more preferably, between about 5% and about 50%, by weight, and generally, most preferably at about 40% by weight Of course as those skilled in the art will recognize, within these parameters the optimum polymer concentration will be influenced by various factors such as the particular polymer employed, the particular metal employed, the particular diagnostic use intended, etc. Preferably, in the case of paramagnetic metals for magnetic resonance imaging, the contrast enhancing metals may be present in a concentration of at least about 0.01% by weight, more preferably between about 0.1% and about 5% by weight, and most preferably between about 0.5% and 0.7% by weight. A preferable concentration of heavy metals for ultrasound or X-ray imaging is at least about 0.1% by weight, more preferably between about 0.5% and about 30% by weight, most preferably between about 5% and about 25% by weight. A preferable concentration of gelling agent, where employed, is at least about 0.5% by weight, more preferably between about 0.5% and about 25% by weight, most preferably between about 5% and about 15% by weight.

The polymers employed in the present invention may, if desired, be phosphorylated such that when these phosphorylated polymers are mixed with contrast enhancing metals or gelling agents such as polyvalent metal cations (e.g., calcium), gels may form more rapidly. In general, higher degrees of polymer phosphorylation result in firmer gels that entrap the contrast enhancing metals more tightly.

Phosphorylation of the polymers may be carried out using conventional techniques which will be readily apparent to those skilled in the art. Specifically, starting with an aliphatic or alicyclic compound containing one or more hydroxyl groups, for example, phosphorylation can be easily carried out by suspending the starting material in chloroform, then adding a phosphoric ester monochloride compound to the suspension, preferably dropwise. Suitable phosphoric ester monochloride compounds include $ClP(O)(OR)_2$, wherein R is selected from $C(O)CH_3$, $C(O)H$, $CH_3$, $C_2H_5$, $C_3H_7$, and $C_4H_9$. The resulting phosphorylated compound can then be treated with water to hydrolyze it to the corresponding phosphoric acid derivatives. Such hydrolyzed derivatives are included within the scope of the phrase phosphorylated compounds herein. Unbound phosphorus may be removed by passing the solution through a column filled anion exchanger. Polymers such as pectin, polygalacturonic acid or polyvinylalcohol may be phosphorylated in such a manner to yield the corresponding phosphorylated derivatives In another method for preparing the phosphorylated aliphatic and alicyclic polymers which may be employed in the invention, urea catalyzed phosphoric acid (or phosphorous acid) phosphorylation procedures may be conveniently utilized. In this procedure, aliphatic or alicyclic compounds are soaked with mixtures of urea and phosphoric acid (or phosphorous acid), then heated to at least 120° C.

In addition, phosphorylation of compounds such as polyvinyl alcohol can be carried out by dissolving polyvinyl alcohol in an organic solvent such as pyridine, dimethylformamide, or dimethylsulfoxide with triethylamine, and then adding dialkyloxyphosphoric monochloride $((RO)_2POCl$, wherein R is a $C_1$–$C_{10}$ alkyl group) to the polymer solution. After phosphorylation, the polymer may then be hydrolyzed by adding water and acidifying with hydrochloric acid. Unbound phosphorous may be removed by passing the solution through a column filled anion exchanger.

Other methods of phosphorylating compounds to produce phosphorylated polymers within the scope of the present invention are disclosed, for example, in Sander et al., *J. Macromol. Sci., Rev, Macromol. Chem.*, Vol. 2, pp. 57–62 (1968), Leonard et al., *J. App. Polymer Sci.*, Vol. 55, pp. 799–810 (1961), Schroeder et al., *J. of Polymer Sci.*, Vol. 47, pp. 417–433 (1960), Kennedy et al., *J. Appl. Chem.*, Vol. 8, pp. 459–464 (1958), Marvel et al., *J. of Polymer Sci.*, Vol. 8, pp. 495–502 (1952), and U.S. Ser. No. 649,437, filed Feb. 1, 1991, the disclosures of each of which are hereby incorporated herein by reference, in their entireties.

If desired, the polymers employed in gel particles may be crosslinked using crosslinking agents known to those skilled in the art, either before or after particularization. Crosslinking may be accomplished by methods known to those skilled in the art. In particular, polymers may be crosslinked by a linker moiety. The structure of such linkers may, for example, be of the following formula:

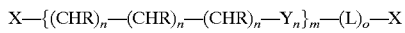

wherein: each R is, independently, H or X; L is a substituted or unsubstituted $C_1$–$C_{20}$alkyl, cycloalkyl, or aryl group; each X is, independently, OH, $NH_2$, NHR, COOH, COOR, SH, epoxide or Z; Y is O, S, CO, N or SiRR; Z is Cl, Br or I; each n is, independently, 0–10; m is 0–10,000; and o is 0–1,000. Linkers may be linked with COOH, OH or $NH_2$ bearing groups on polymers by using condensation agents, for example, dicylohexylcarboimide (DCC) For example, formaldehyde, glyoxal, epichlorhydrin, dimethyldichlorosilane, diepoxybutane and β,β-dichloroethylsulfide may be used to crosslink gel particles of the present invention. Treatment with formaldehyde, for example, leads to crosslinkages between secondary hydroxyl groups to form mainly intermolecular methylene bridges Crosslinking between carboxyl groups may be formed by agents such as diepoxybutane and β,β-dichloroethylsulfide. Sulfur containing cross-linkers may be used if desired, so as to be readily degradable within the body. Such cross-linkers include but are not limited to dithiobis(succinimidylpropionate) (DSP) and 3,3'-dithiobis (sulfosuccinimidylpropionate) (DTSSP) Other procedures for cross-linking the polymers of the invention will be readily apparent to those skilled in the art, and include, for example, Staros, *Biochemistry*, Vol. 21, pp. 3950–3955 (1982), Lomant et al., *J. Mol. Biol.*, Vo. 104, pp. 243–261 (1976), Vollmert, *Polymer Chemistry*, pp. 1–8, 541–561, Springer-Verlag, New York, N.Y. (1973), and Odian, *Principles of Polymerization*, pp. 1–39, 96–112, and 611–614, McGraw-Hill Co., N.Y., N.Y. (1970), the disclosures of each of which are hereby incorporated herein by reference in their entirety. Crosslinking of the polymers is optionally employed, and is generally carried out for the purpose of increasing the stability of the gels and prolonging the in vivo transit time. For example, such cross-linking may prolong the circulation or staying time of the gels within the patient in, for example, intravascular imaging or imaging of the gastrointestinal tract. Such cross-linking is not preferred, however, since it has been found that the degree of tissue inflammation and patient discomfort tends to increase with the use of cross-linked polymers. Thus, for the purpose of the present invention it is preferable that the polymers are not cross-linked, that is, are non-crosslinked polymers, although, of course, cross-linking may be employed, if desired, in accordance with the present invention.

Polymers may also, if desired, be modified prior or subsequent to gelation or particularization, such as by the incorporation of targeting agents on their surface and in other ways that will be readily apparent to those skilled in the art. For example, agents such as antibodies, proteins, carbohydrates, and lectins may be incorporated on the polymeric surface of gel particles. These targeting agents may be useful for example, for localizing gel particles to target regions or organs. For example, Fab'2 fragments of antibodies may be covalently bound to the surface of the gels, such as through amide linkages from amino groups of the antibodies to the carboxylic acids groups on the polymers (e.g., polygalacturonic acid). Similarly, other synthetic or natural peptides may be so attached. Alternatively, the carboxylic acid groups of proteins (e.g., antibodies or peptides) may be attached to amide or thiol groups on the polymers of the gels. The resulting labelled gel particles may then be used for imaging specific tissues. For example, fragments of antileukocyte antigen antibody covalently bound to gel contrast media may be used to detect metastases from colonic carcinoma. As one skilled in the art would recognize, once armed with the tools of the present invention, there are numerous possibilities for using the subject gels for targeted site-specific imaging.

Also encompassed by the present invention are diagnostic kits comprising gel particles in combination with conventional diagnostic kit components such as buffering agents, antibacterial agents, stabilizing agents or excipients. Such components are well known in the art, and are discussed, for example, in *The United States Pharmacopeia—The National Formulary*, 22nd Revision, Jan. 1, 1990, Hack Publishing Company, Easton, Pa., *Remington's Pharmaceutical Sciences*, Gennaro, A. R, ed., Hack Publishing Company, Easton, Pa. (1985), the disclosures of each of which are hereby incorporated herein by reference in their entirety.

The present invention is useful in imaging a patient generally, and/or in specifically diagnosing the presence of diseased tissue in a patient. The imaging process of the present invention may be carried out by administering a contrast medium of the present invention to a patient, and then scanning the patient using ultrasound, X-ray or magnetic resonance imaging to obtain visible images of an internal region of a patient and/or of any diseased tissue in that region. By region of a patient, it is meant the whole patient or a particular area or portion of the patient. The contrast media of the invention are particularly useful in providing images of the liver. The subject contrast media are also particularly suited to imaging the gastrointestinal region and the vasculature. The phrase gastrointestinal tract, as used herein, includes the region of a patient defined by the esophagus, stomach, small and large intestines and rectum. The phrase vasculature, as used herein, denotes the blood vessels in the body or in an organ or part of the body. The patient can be any type of mammal, but most preferably is a human.

As those skilled in the art will recognize, administration may be carried out in various fashions, such as intravascularly, orally, rectally, etc., using a variety of dosage forms. When the region to be scanned is the gastrointestinal region, administration of the contrast medium of the invention is preferably carried out orally or rectally. Alternatively, when the vasculature such as the vasculature of the liver is being scanned, the preferred mode of administration is intravascular administration. The useful dosage to be administered and the particular mode of administration will vary depending upon the age, weight and the particular mammal and region thereof to be scanned, the type of scanning and the particular medium of the invention to be employed. Typically, dosage is initiated at lower levels and increased until the desired contrast enhancement is achieved.

As those skilled in the art will recognize, various combinations of polymers, contrast enhancing metals, and gelling agents may be used, depending on such factors as the imaging modality employed, the type of mammal, the area to be imaged, and the particular diagnosis desired. In carrying out the method of the present invention, the contrast medium can be used alone, or in combination with other diagnostic, therapeutic or additional agents. Such additional agents include excipients such as flavoring, coloring, stabilizing agents, thickening materials, osmotic agents and antibacterial agents. Such agents may enhance the contrast media's use in vitro, the stability of the composition during storage, or other properties important to achieving optimal effectiveness. The contrast media of the present invention may also be sterilized prior to use by, for example, autoclaving, if desired.

The magnetic resonance imaging techniques which are employed are conventional and are described, for example, in Kean, D. M., and N. A. Smith, *Magnetic Resonance Imaging: Principles and Applications* (William and Wilkins, Baltimore 1986), the disclosures of which are hereby incorporated herein by reference in their entirety. Contemplated magnetic resonance imaging techniques include, but are not limited to, nuclear magnetic resonance (NMR) and electronic spin resonance (ESR). Likewise, ultrasound techniques are carried out by conventional procedures known to those skilled in the art, such as those disclosed in Brown, R. E., *Ultrasonography, Basic Principles and Clinical Applications* (Warren H. Green, Inc., St. Louis, Mo. 1975) the disclosures of which are hereby incorporated herein by reference in their entirety. For example, with regard to ultrasound imaging, such imaging may be performed with an Acuson 128 Scanner (Milpitas, Calif.) using a 7.5 megahertz linear array transducer. The post processing function may be linear with pre-processing set at 0 and persistence at 2. Multifocal zones with a decreased frame rate can be used for most images. X-ray imaging is also conventional, and includes such X-ray imaging techniques as computed tomography (CT), such as those described in *Computed Body Tomography*, Lee, J. K. T., Sagel, S. S., and Stanley, R. J., eds., Ch. 1, pp. 1–7, (Raven Press, New York 1933). These and other imaging techniques are also described in Squire, L. F., H. D., *Fundamentals of Radiology* (Harvard University Press, Cambridge, Mass. 1982), the disclosures of which are hereby incorporated herein by reference in their entirety. Although any of a variety of imaging techniques may be employed, the preferred imaging modality is magnetic resonance imaging, specifically nuclear magnetic resonance imaging. As will be apparent to those skilled in the art, for magnetic resonance imaging purposes the gel particles may operate as T1, T2 or proton density contrast medium, depending upon the type of polymer used, the molecular weight of the polymer, the concentration of the polymer, the type of metal ions mixed with the polymer, the type of MRI modality used, and the details of the pulse sequence employed for MRI imaging, and all such mechanisms of operation are considered to be within the ambit of the present invention.

The gel particles of the present invention have been shown to be extremely useful as contrast enhancement media. By employing the gel particles in accordance with the present invention, lower overall concentration of the contrast enhancing metals may be used to achieve the same, or in many cases a better degree of, contrast enhancement results. This has benefits not only in terms of toxicity, by avoiding the use of large amounts of the potentially toxic metal ions, but also in terms of cost, since less of the often more expensive conventional metal ions are used. Further, because of the entrapment of the contrast enhancing metals in the polymer matrix, the potentially toxic metal ions have less of an opportunity to be released and exhibit any toxic side effects. These and other advantages will be readily apparent to those skilled in the art, upon reading the present disclosure.

The present invention is further described in the following examples. In all of the examples, as well as throughout the present specification, all molecular weights are weight average molecular weights. The examples which follow are not to be construed as limiting the scope of the appended Claims.

EXAMPLE 1

Preparation of Polygalacturonic, Manganese and Calcium Gels

For preparation of the polygalacturonic acid, manganese and calcium gel contrast medium, 4.4 grams of polygalacturonic acid (poly-G) (Fluka, Ronkonkoma, N.Y.) was added to about 200 ml of deionized water, and the pH raised to a pH of 6.5 with sodium bicarbonate (30 ml 1 M sodium bicarbonate) at room temperature. The poly-G was then placed into a blender (commercial household blender), after which 680 mg of $Mn^{+2}$ was added as 24.5 ml of a 0.5 M $MnCl_2$ stock solution. A clear inhomogeneous gel formed. The gel was blended on a liquify setting for 3 minutes after which time 250 mg $Ca^{+2}$ was added by the addition of 9.2 ml of a $CaCl_2$ solution. The resulting white gel was blended for 4 minutes on a liquify setting until homogenous and rather thin. The solution was then removed from the blender and the volume was brought up to 250 ml volumetrically with deionized water. The solution was returned to the blender and mixed on a liquify setting for 2 minutes to homogenize the solution. The solution was then extruded via an Extruder Device (Lipex Biomembranes, Vancouver, B.C. Canada) through filters having pore sizes from 2000 nanometers to 15 nanometers (sequentially downsizing the filters) to produce nanogel contrast media of the present invention.

EXAMPLE 2

Preparation of Pectin, Manganese and Optionally Calcium Gels

Two types of contrast media were prepared using purple and red low methoxy pectin: (1) 60 mg of $Mn^{+2}$ with 1 gram of pectin (Spreda Corps, Prospect Ky.); and (2) 60 mg $Mn^{+2}$ with 1 gram of pectin and 10 mg $Ca^{+2}$. Purple and red pectin designate different types of low methoxy pectin sold by Spreda Corporation. Red pectin contains about 35 to about 40% methoxylation (esterification), whereas purple pectin contains about 33 to about 38% methoxylation (esterification).

1% Red Pectin and 0.6% $Mn^{+2}$

One gram of pure red pectin was dissolved in 100 ml deionized water. Sixty mg of $Mn^{+2}$ was added as 2.16 ml of a 500 mM $MnCl_2$ stock solution. The solution was then blended on a liquify setting for thirty seconds and extruded through filters having pore sizes of 200, 100, 50, and 30 nm (sequentially downsizing the filters) to produce nanogel contrast media of present invention.

1% Red Pectin, 0.6% $Mn^{+2}$ and 0.1% $Ca^{+2}$

One gram of pure red pectin was dissolved in 100 ml deionized water. Sixty mg of $Mn^{+2}$ was added as 2.16 ml of 500 mM $MnCl_2$ stock solution. An inhomogeneous suspension resulted. To this suspension 10 mg of $Ca^{+2}$ was added as 0.036 g of $CaCl_2$. The gel was still inhomogeneous. The solution was then blended on a liquify setting for 1 minute. A thick, homogeneous gel resulted. The sample was extruded through filters having pore sizes of 200, 100, 50 and 15 nm (sequentially downsizing the filters) to produce nanogel contrast media of the present invention.

1% Purple Pectin, 0.6% $Mn^{+2}$

One gram of pure purple pectin was dissolved in 100 ml deionized water. Sixty mg of $Mn^{+2}$ was added to the solution as 2.16 ml of 500 mM MnCl stock solution. The resulting gel was then blended on a liquify setting for thirty seconds. A thick nonhomogeneous gel was formed. The gel was extruded through filters having pore sizes of 200, 100, 50, 30 and 15 nm (sequentially downsizing the filters) to produce nanogel contrast media of the present invention.

1% Purple Pectin, 0.6% $Mn^{+2}$, 0.1% $Ca^{+1}$

One gram of pure purple pectin was dissolved in 100 ml of water. Sixty milligrams of $Mn^{+2}$ was added to the solution as 2.16 ml of a 500 Mm $MnCl_2$ stock solution. The resulting suspension was blended on a liquify setting for 30 seconds. 10 mg of $Ca^{+2}$ was then added as 0.036 g of solid $CaCl_2$. Subsequently, the solution was blended on a liquify setting for 1 minute. A thick tan gel resulted. The gel was extruded through filters having pore sizes 200, 100, 50 and 15 nm (sequentially downsizing the filters) to produce nanogel contrast media of the present invention.

EXAMPLE 3

Preparation of Polygalacturonic Acid and Ferrous Gels

The contrast medium was prepared by adding 3.3 g of polygalacturonic acid (poly-G) to 150 ml of deionized water and raised to a pH of 6.0 with sodium bicarbonate (30 ml of 1 M sodium bicarbonate) at room temperature. The poly-G was then put into a blender, after which 2.49 g of ferrous iron (as solid $FeCl_2$) was added. A yellow inhomogeneous gel formed. The gel was then blended on a liquify setting for 2 minutes until the resulting yellow/green gel was homogenous and rather thin. Next, the solution was brought up to 250 ml volumetrically with deionized water, returned to the blender and mixed on a liquify setting for 2 minutes to homogenize the solution. The solution was then extruded via an Extruder Device (Lipex Biomembranes, Vancouver, B.C., Canada) through filters having pore sizes of 200, 100, 50, 30 and 15 nanometers in mean diameter (sequentially downsizing the filters) to produce nanogel contrast media of the present invention.

EXAMPLE 4

Preparation of Polygalacturonic Acid Manganese and Sucrose Gels

The gel was prepared by adding 1.5 grams of polygalacturonic acid to 150 ml of deionized water. Sodium bicarbonate was added to raise the pH to 6.0. Fifty grams of sucrose was then added and the solution was blended on a liquify setting for 20 seconds. Manganese ion ($Mn^{+2}$) 680 mg was then added as 24.5 ml 0.5 H $MnCl_2$ stock. The solution was blended on a liquify setting and brought up to 250 ml volumetrically by the addition of deionized water. The solution was returned to the blender and blended on a liquify setting for 20 seconds to homogenize the solution. The solution was extruded via the Extruder Device (Lipex Biomembranes, Vancouver, B.C., Canada) through filters having pore sizes of 200, 100, 50, 30 and 15 nanometers (sequentially downsizing the filters) to produce nanogel contrast media of the present invention.

EXAMPLE 5

Measurement of Cation Concentration

Samples prepared substantially in accordance with Examples 1 through 4 were dialyzed for 24 hours in SPECTRA/POR Ce (cellulose ester) Membrane, molecular weight cutoff 100 (Spectrum Medical Industries Inc., Los Angeles Calif.) against 5% propylene glycol in normal saline The samples were then spectrophotometrically analyzed for cation concentration (i.e., $Mn^{+2}$) following dialysis, using a Milton Roy Spectronic 20D variable wavelength spectrophotometer (Rochester, N.Y.). Cation concentrations were as shown in Table 1 In Table 1, PG denotes polygalacturonic acid (Poly-G).

TABLE 1

| | Concentration | |
|---|---|---|
| Molar ratio PG/Mn/Ca | Mn Concentration (post dialysis and sizing) | % Mn Retention |
| 100/10/10 | 0.25 mM | 2.5% |
| 4/1/0.5 | 0.332 mM | 1.32% |
| 4/2/1 | 5.175 mM | 20.7% |
| 4/2/2 | 6.22 mM | 25% |
| 20% Sucrose Gel | 8.22 mM | 23.5% |

EXAMPLE 6

Preparation of Low Molecular Weight Poly-G from Low Methoxy Pectin

Preparation

Ten grams of DO75-X Apple Pectin (Spreda Corp., Prospect, Ky.), a low methoxy pectin, was hydrolyzed in 100 ml of a 5% HCl solution for 5 hours at a constant temperature of 85° C. The solution was then vacuum filtered, resulting in a dark brown precipitate and a yellow-colored solution. The dark brown precipitate (Sample 1) was set aside The solution was taken and subjected to a decolorization step by adding two grams of activated charcoal to the solution and heating the solution to 80° C. for 30 minutes. The solution was then filtered, resulting in a clear colorless liquid. Next, the solution was evaporated to dryness, yielding a yellow-brown powder (Sample 2), which was low molecular weight polygalacturonic acid (Poly-G), as shown in Table 2 (last entry) The Poly-G is suitable for use in preparing a gel particle contrast medium of the invention.

Molecular Weight Analysis

All HPLC analyses were done on a Binary Liquid Chromatography Pump, Model No. 250 (Perkin Elmer, Norwalk, Conn.), using the Diode Array Detector, Model No. 135 (Perkin Elmer). The data were processed on a Personal Integrator, Model No. 1020 (Perkin Elmer). Detector settings were lambda A 245 and lambda B 280. Run time was 20 minutes at a flow rate of 1 ml/minute. All samples were passed through a Biogel Sec 40 XL size exclusion chromatography column (Bio Rad Laboratories, Richmond, Calif.). The resultant data is set forth in Table 2.

TABLE 2

High Pressure Liquid Chromatography Analysis of Molecular Weight

| MW and Source | RT* |
|---|---|
| Commercial Poly-G (MW range 25,000–50,000) | 5.33 |
| Commercial mono galacturonic acid (MW 194) | 9.04 |
| Deca galacturonic acid (MW ≈ 2,200) | 8.50 |
| Low molecular weight Poly-G** | 7.90 |

*Shows column retention time in minutes; shorter retention time indicates larger molecular weight polymer.
**Hydrolyzed from pectin (See "Preparation", above).

As shown by Table 2, commercially available Poly-G (Fluka, Ronkonknoma, N.Y.) which is known to be comprised of a mixture of polymers of Poly-G with molecular weights ranging from 25,000 to 50,000 has a retention time on the column of 5.33 minutes. Commercially available mono-galacturonic acid (molecular weight 194), has the longest retention time, a retention time of 9.04 minutes. Deca galacturonic acid (prepared by the method described in Lakatos et al., U.S. Pat. No. 4,225,592 issued Sep. 30, 1980, hereinafter referred to as Lakatos, the disclosures of which are hereby incorporated herein by reference in their entirety), has a molecular weight of approximately 2,200 and was found to have a retention time of 8.50 minutes. Comparing the retention times with that of commercial Poly-G, commercial galacturonic acid monomer and deca galacturonic acid described in Lakatos, reveals that the Poly-G hydrolyzed from pectin (Sample 2, as described in "Preparation" above), is low molecular weight Poly-G. Specifically, the Poly-G from Sample 2 has a retention time of 7.9 minutes, indicating a MW range near that of deca galacturonic acid (≈2,200 dalton). Evaluation of the dark brown precipitate (Sample 1) showed a retention time of 5.53 minutes (data not shown)—almost identical to that of high molecular weight Poly-G.

EXAMPLE 7

Relaxivity of Various Polymers and Manganese

Contrast media of the invention, prepared substantially in accordance with the procedures in Examples 1, 2, 3, 4 and 5, were analyzed for relaxivity and compared with the relaxivity of other samples. Samples A through D are provided for comparative purposes only. All samples were analyzed for relaxivity using a Toshiba 0.5 T clinical MR magnet. Samples E through J are gel particle contrast media within the scope of the invention. Samples A through D are provided for comparative purposes only. Table 3 below shows the relaxivity of the various samples.

TABLE 3

| SAMPLE | $R_1$ (1/T1 mmol sec$^{-1}$) | $R_2$ (1/T2 mmol sec$^{-1}$) |
|---|---|---|
| A. Mn-EDTA-MEA | 3.04 ± 0.15 | 7.98 ± 0.23 |
| B. Mn-Poly-EDTA-EOEA-DP | 6.48 ± 0.01 | 12.26 ± 0.05 |
| C. MnCl$_2$ | 8.730 ± 0.903 | 39.45 ± 0.515 |
| D. MnCl$_2$, Galacturonate Monomer | 9.01 ± 0.41 | 37.36 ± 0.10 |
| E. Pectin D-075X, Mn | 16.53 ± 0.88 | 36.53 ± 0.69 |
| F. MnCl$_2$, Algin | 20.3 ± 1.948 | 40.20 ± 0.38 |
| G. Poly-G, Mn | 28.99 ± 0.562 | 55.31 ± 1.11 |
| H. 100% Deca Poly-G, Mn | 35.33 ± 0.623 | 61.02 ± 0.886 |
| I. 40% Deca Poly-G, 60% Normal Poly-G, Mn | 42.62 ± 0.289 | 67.28 ± 0.459 |
| J. Hydrolyzed Pectin Mn | 46.11 ± 0.347 | 67.98 ± 1.256 |

As shown by the data, manganese ion ($Mn^{+2}$) as the free ion manganese chloride has an $R_1$ and $R_2$ of about 8 and 39 per millimole/sec$^{-1}$ respectively (Sample C). In comparison with Sample C, the chelates (Samples A and B) showed reduce relaxivity. Specifically, the polymeric chelate Mn-Poly-EDTA-EOEA-DP has an $R_1$ and $R_2$, respectively, of about 6 and 13 (Sample B) and the simple chelate Mn-EDTA-MEA has an $R_1$ and $R_2$, respectively, of about 3 and 8 (Sample A). The monomer of galacturonate has no appreciable effect on the relaxivity of manganese (Sample D). The contrast media of the invention, however, have a large effect on the relaxivity of manganese. For example, red pectin (D-075X, low methoxypectin, Spreda Corp., Prospect, Ky.) (Sample E), and algin (Sample F) appreciably increase the relaxivity of manganese As also shown by the data in Table 3, different preparations of Poly-G within the scope of the invention show still greater relaxivity. Most effective are low molecular weight polygalacturonates. For example, hydrolyzed pectin prepared according to Example 5 had an $R_1$ and $R_2$ relaxivity of 46 and 68, respectively (Sample J). A mixture of 40% deca Poly-G prepared according to Example 5 and 60% normal Poly-G obtained from Fluka (MW 22,000 to 50,000) (Sample I) has relaxivity greater than pure deca Poly-G (Sample H). These data show that optimal relaxivity is achieved for manganese in admixture with Poly-G below about 5,000 MW.

EXAMPLE 8

Stability of Poly-G, Manganese and Sucrose Gel

The stability of gel particles in retaining manganese was tested by dialyzing the gel particles for 24 hours in a SPECTRA/POR Ce (cellulose ester) Membrane, molecular weight cut off 100 (Specturm Medical Industries, Inc., Los Angeles, Calif.) against various solutions The gel particles of the invention show retention of manganese upon prolonged dialysis, evidence of the good stability of compounds of the invention. Specifically, as Table 4 shows, between 22% and 52% of the manganese is retained after 24 hours, for gel particles prepared in accordance with Example 4. After the first 24 hours of dialysis where some unbound manganese is removed, the particles were found to retain the remaining manganese even after prolonged dialysis (e.g. greater than 72 hours of dialysis) (data not shown).

TABLE 4

Effect of Dialysis on Poly-G Mn Sucrose Gels

| Time (hrs.) | Dialyzed in 5% Propylene Glycol Saline | Dialyzed in Saline | Dialyzed in 20% Sucrose in Deionized Water |
|---|---|---|---|
| 0 | 100% | 100% | 100% |
| 24 | 52% | 42% | 22% |

EXAMPLE 9

Stability and Relaxivity of Manganese in Polygalacturonic Acid Gels

Contrast media of the invention, prepared substantially in accordance with the procedures of Examples 1, 3 and 4, were analyzed for relaxivity and for stability on dialysis. Table 5 shows the percent retention and relaxivity of manganese by gel particles prepared in accordance with the invention. The gel comprising polygalacturonic acid (Poly-G; PG), manganese, and sucrose exhibits the highest relaxivity and retention of manganese.

TABLE 5

$Mn^{+2}$ $Ca^{+2}$ Poly-G, $Mn^{+2}$ Sucrose Poly-G, and $Fe^{+2}$ Poly G Gels In Vitro Relaxivity and $Mn^{+2}$ Retention

| Sample | % $Mn^{+2}$ Retention | $R_1$ | $R_2$ |
|---|---|---|---|
| PG/Mn/Ca 4/2/1 ratio | 20.7 | 0.760 ± 0.161 | 1.46 ± 0.046 |
| PG/Mn/Ca 10/1/1 ratio | 2.5 | 10.44 ± 0.356 | 11.86 ± 1.65 |
| PG/Mn/Ca 4/1/0.5 ratio | 1.33 | 3.57 ± 0.238 | 12.32 ± 1.29 |
| PG/Mn/Ca 4/2/2 ratio | 24.0 | 0.163 ± 0.015 | 0.407 ± 0.083 |
| PG/$Fe^{+2}$ | — | 0.109 ± 0.004 | 0.138 ± 0.014 |
| PG + Mn + 20% Sucrose | 23.5 | 24.49 ± 4.85 | 117.9 ± 0.983 |

EXAMPLE 10

In Vivo Imaging Data

Shown in the Tables 6 through 9 are NMR imaging data from four rats injected intravenously with doses of 2.33 to 2.5 micromoles/kg of manganese and polygalacturonic acid (Poly-G; PG) or pectin gel particles and scanned via NMR. Tables 6 and 7 are data from intravenous injections of contrast medium comprising gel particles prepared substantially in accordance with Example 1. Table 8 is data from intravenous injections of contrast media comprising gel particles prepared substantially in accordance with Example 2. Table 9 is data from intravenous injections of contrast media comprising gel particles prepared substantially in accordance with Example 4. As shown by the data, enhancement by gel particles prepared by gelation of Poly-G and manganese with calcium showed some enhancement. Better enhancement was observed with red pectin and manganese gels. The greatest enhancement is observed with the gel particles prepared by gelation of Poly-G and manganese with sucrose

TABLE 6

PG/Mn/Ca 4/2/1
2.5 μmoles $Mn^{+2}$/kg

| | Liver Signal Intensity | Percent Enhancement* of the Liver |
|---|---|---|
| Pre Contrast | 169 ± 11 | |
| 5 Min Post Contrast | 190 ± 15 | 12.4% |
| 15 Min Post Contrast | 189 ± 12 | 11.8% |
| 25 Min Post Contrast | 202 ± 5.3 | 19.5% |
| 60 Min Post Contrast | 140 ± 11 | No change |

*Percent enhancement = [(signal intensity post-contrast agent − signal intensity pre-contrast agent)/(signal intensity pre-contrast agent)] × 100.

TABLE 7

PG/Mn/Ca 4/2/2
2.5 μmoles $Mn^{+2}$/kg

| | Liver Signal Intensity | Percent Enhancement* of the Liver |
|---|---|---|
| Pre Contrast | 169 ± 13 | |
| 5 Min Post Contrast | 166 ± 11 | No change |
| 15 Min Post Contrast | 175 ± 14 | 3.5% |
| 25 Min Post Contrast | 169 ± 8.8 | No change |
| 60 Min Post Contrast | 152 ± 11 | No change |

*Percent enhancement = [(signal intensity post-contrast agent − signal intensity pre-contrast agent)/(signal intensity pre-contrast agent)] × 100.

TABLE 8

Red Pectin + Mn
2.5 μmoles $Mn^{+2}$/kg

| | Liver Signal Intensity | Percent Enhancement* of the Liver |
|---|---|---|
| Pre Contrast | 157 ± 14 | |
| 5 Min Post Contrast | 169 ± 11 | 7.6% |
| 15 Min Post Contrast | 169 ± 10 | 7.6% |
| 25 Min Post Contrast | 205 ± 11 | 30.6% |
| 60 Min Post Contrast | 211 ± 13 | 34.4% |

*Percent enhancement = [(signal intensity post-contrast agent − signal intensity pre-contrast agent)/(signal intensity pre-contrast agent)] × 100.

TABLE 9

PG Mn 20% Sucrose
2.33 μmoles $Mn^{+2}$/kg

| | Liver Signal Intensity | Percent Enhancement* of the Liver |
|---|---|---|
| Pre Contrast | 139 ± 12 | |
| 5 Min Post Contrast | 226 ± 14 | 62.5% |
| 15 Min Post Contrast | 216 ± 12 | 55.4% |

TABLE 9-continued

PG Mn 20% Sucrose
2.33 μmoles Mn$^{+2}$/kg

| | Liver Signal Intensity | Percent Enhancement* of the Liver |
|---|---|---|
| 25 Min Post Contrast | 216 ± 9 | 55.4% |
| 60 Min Post Contrast | 235 ± 7 | 69.1% |

*Percent enhancement = [(signal intensity post-contrast agent − signal intensity pre-contrast agent)/(signal intensity pre-contrast agent)] × 100.

EXAMPLE 11

In Vivo Imaging Data

Table 10 represents enhancement of the liver using polygalacturonic acid manganese sucrose gel particles prepared substantially in accordance with Example 4 in three studies. As the data indicates, enhancement is increased from 40 to 50% by the use of the gel particles.

TABLE 10

Polygalacturonic Acid Manganese Sucrose Gels
% Enhancement* of the Liver

| Study | Post Contrast | 20 Min. Post Contrast |
|---|---|---|
| 3 μmoles/kg | 51% | 49% |
| 5 μmoles/kg | 44% | 36% |
| 5 μmoles/kg | 51% | 42.4% |

*Percent enhancement = [(signal intensity post-contrast agent − signal intensity pre-contrast agent)/(signal intensity pre-contrast agent)] × 100.

EXAMPLE 12

In Vivo Liver to Tumor Contrast to Noise

Table 11 provides data of three tests of contrast to noise. Contrast to noise was approximately double in tests using poly-G manganese sucrose gels prepared substantially in accordance with Example 4. Contrast to noise was calculated by measuring the signal intensity of the liver, subtracting the signal intensity of the tumor, and dividing this by the standard deviation of the background noise.

TABLE 11

Polygalacturonic Acid, Manganese And Sucrose Gels
Liver to Tumor Contrast to Noise

| Study | Pre Contrast | Post Contrast | 20 Min Post Post Contrast |
|---|---|---|---|
| 3 μmoles/kg | 44 | 84 | 90 |
| 5 μmoles/kg | 63 | 122 | 102 |
| 5 μmoles/kg | 66 | 134 | 105 |

EXAMPLE 13

Signal Intensity

Tables 12 and 13 provide data from tests of signal intensity in the heart, kidney/medulla and kidney/cortex All tests show an increase in signal intensity in tests using gel particles prepared substantially in accordance with Example 4. Signal intensity increased only slightly in the heart, but increased more significantly in the kidney/medulla, and most substantially in the kidney/cortex

TABLE 12

Signal Intensity
Heart

| Study | Pre Contrast | Post Contrast | 20 Min Post Post Contrast |
|---|---|---|---|
| 3 μmoles/kg | 86 ± 7 | 87 ± 7 | 89 ± 8 |
| 5 μmoles/kg | 79 ± 9 | 84 ± 2 | 81 ± 6 |
| 5 μmoles/kg | 75 ± 6 | 82 ± 6 | 93 ± 6 |

TABLE 12

Signal Intensity

| Study | Pre Contrast | Post Contrast | 20 Min Post Post Contrast |
|---|---|---|---|
| | Kidney/Medulla | | |
| 3 μmoles/kg | 66 ± 6 | 88 ± 6 | 78 ± 9 |
| 5 μmoles/kg | 79 ± 8 | 95 ± 6 | 78 ± 4 |
| 5 μmoles/kg | 77 ± 5 | 84 ± 12 | 82 ± 5 |
| | Kidney/Cortex | | |
| 3 μmoles/kg | 102 ± 5 | 154 ± 12 | 159 ± 5 |
| 5 μmoles/kg | 126 ± 7 | 163 ± 12 | 164 ± 10 |
| 5 μmoles/kg | 130 ± 7 | 160 ± 3 | 163 ± 8 |

Various modifications of the invention in addition to those shown and described herein will be apparent to those skilled in the art from the foregoing description Such modifications are also intended to fall within the scope of the appended Claims.

What is claimed is:

1. A method of providing an image of an internal region of a patient comprising (i) administering to the patient a contrast medium comprising watery gel particles of less than about 90μ in mean diameter, said watery gel particles comprising at least one methoxylated natural or methoxylated modified natural polymer entrapping at least one contrast enhancing metal, and (ii) scanning the patient using magnetic resonance imaging to obtain visible images of a region.

2. A method for diagnosing the presence of diseased tissue in a patient comprising (i) administering to the patient a contrast medium comprising watery gel particles of less than about 90μ in mean diameter, said watery gel particles comprising at least one methoxylated natural or methoxylated modified natural polymer entrapping at least one contrast enhancing metal, and (ii) scanning the patient using magnetic resonance imaging to obtain visible images of any diseased tissue in the patient.

3. A method of providing an image of an internal region of a patient comprising (i) administering to the patient a contrast medium comprising firm gel particles of less than about 90μ in mean diameter, said firm gel particles comprising at least one synthetic polymer entrapping at least one contrast enhancing metal ion, wherein said synthetic polymer is selected from the group consisting of polyethylenes, polypropylenes, polyurethanes, pluronic acids, pluronic alcohols, polyvinyls, nylon, polystyrene, fluorinated hydrocarbons, fluorinated carbons, polyacrylates, polyacrylic acids and polyacrylamides, and (ii) scanning the patient using magnetic resonance imaging to obtain visible images of the region.

4. A method for diagnosing the presence of diseased tissue in a patient comprising (i) administering to the patient a contrast medium comprising firm gel particles of less than about 90µ in mean diameter, said firm gel particles comprising at least one synthetic polymer entrapping at least one contrast enhancing metal ion, wherein said synthetic polymer is selected from the group consisting of polyethylenes, polypropylenes, polyurethanes, pluronic acids, pluronic alcohols, polyvinyls, nylon, polystyrene, fluorinated hydrocarbons, fluorinated carbons, polyacrylates, polyacrylic acids and polyacrylamides, and (ii) scanning the patient using magnetic resonance imaging to obtain visible images of any diseased tissue in the patient.

5. A method of providing an image of an internal region of a patient comprising (i) administering to the patient a contrast medium comprising firm gel particles of less than about 90µ in mean diameter, said firm gel particles comprising at least one unmethoxylated natural or unmethoxylated modified natural polymer entrapping at least one contrast enhancing metal ion, and (ii) scanning the patient using magnetic resonance imaging to obtain visible images of the region, wherein said polymer is non-crosslinked and said firm gel particles contain substantially no chelates.

6. A method for diagnosing the presence of diseased tissue in a patient comprising (i) administering to the patient a contrast medium comprising firm gel particles of less than about 90µ in mean diameter, said firm gel particles comprising at least one unmethoxylated natural or unmethoxylated modified natural polymer entrapping at least one contrast enhancing metal ion, and (ii) scanning the patient using magnetic resonance imaging to obtain visible images of any diseased tissue in the patient, wherein said polymer is non-crosslinked and said firm gel particles contain substantially no chelates.

7. A method of claim 6 wherein said unmethoxylated polymer is selected from the group consisting of arabinans, fructans, fucans, galactans, galacturonans, glucans, mannans, xylans, levan, fucoidan, carrageenan, galactocarolose, pectins, pectic acids, amylose, pullulan, glycogen, pustulan, chitin, keratin, chondroitin, dermatan, hyaluronic acid, alginic acid, xanthan gum, polypeptides, polyalcohols, copolymers containing glucose, and polysaccharides containing at least one aldose, ketose, acid or amine selected from the group consisting of erythrose, threose, ribose, arabinose, xylose, lyxose, allose, altrose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid.

8. A method of claim 7 wherein said unmethoxylated polymer is selected from the group consisting of arabinans, fucans, galactans, galacturonans, mannans, xylans, fucoidan, carrageenan, galactocarolose, pectins, pectic acids, amylose, pustulan, chitin, keratin, chondroitin, dermatan, hyaluronic acid, alginic acid, xanthan gum, polypeptides, polyalcohols, copolymers containing glucose, and polysaccharides containing at least one aldose, ketose, acid or amine selected from the group consisting of erythrose, threose, ribose, arabinose, xylose, lyxose, allose, altrose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid.

9. A method of claim 8 wherein said unmethoxylated polymer is selected from the group consisting of hyaluronic acid and alginic acid.

10. A method of claim 6 wherein said contrast enhancing metal ion is selected from the group consisting of paramagnetic metal ions and heavy metal ions.

11. A method of claim 10 wherein said contrast enhancing metal ion is a paramagnetic metal ion selected from the group consisting of gadolinium, manganese, copper, chromium, iron, cobalt, erbium, nickel, europium, technetium, indium, samarium, dysprosium, ruthenium, ytterbium, yttrium, and holmium ions and combinations thereof.

12. A method of claim 6 wherein said unmethoxylated polymer is selected from the group consisting of arabinans, fructans, fucans, galactans, galacturonans, glucans, mannans, xylans, levan, fucoidan, carrageenan, galactocarolose, pectins, pectic acids, amylose, pullulan, glycogen, pustulan, chitin, keratin, chondroitin, dermatan, hyaluronic acid, alginic acid, xanthan gum, polypeptides, polyalcohols, copolymers containing glucose, and polysaccharides containing at least one aldose, ketose, acid or amine selected from the group consisting of erythrose, threose, ribose, arabinose, xylose, lyxose, allose, altrose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid.

13. A method of claim 12 wherein said unmethoxylated polymer is selected from the group consisting of arabinans, fucans, galactans, galacturonans, mannans, xylans, fucoidan, carrageenan, galactocarolose, pectins, pectic acids, amylose, pustulan, chitin, keratin, chondroitin, dermatan, hyaluronic acid, alginic acid, xanthan gum, polypeptides, polyalcohols, copolymers containing glucose, and polysaccharides containing at least one aldose, ketose, acid or amine selected from the group consisting of erythrose, threose, ribose, arabinose, xylose, lyxose, allose, altrose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid.

14. A method of claim 13 wherein said unmethoxylated polymer is selected from the group consisting of hyaluronic acid and alginic acid.

15. A method of claim 5 wherein said contrast enhancing metal ion is selected from the group consisting of paramagnetic metal ions and heavy metal ions.

16. A method of claim 15 wherein said contrast enhancing metal ion is a paramagnetic metal ion selected from the group consisting of gadolinium, manganese, copper, chromium, iron, cobalt, erbium, nickel, europium, technetium, indium, samarium, dysprosium, ruthenium, ytterbium, yttrium, and holmium ions and combinations thereof.

17. A method of claim 4 wherein said synthetic polymer is non-crosslinked.

18. A method of claim 4 wherein said contrast enhancing metal ion is selected from the group consisting of paramagnetic, metal ions and heavy metal ions.

19. A method of claim 18 wherein said contrast enhancing metal ion is a paramagnetic metal ion selected from the group consisting of gadolinium, manganese, copper, chromium, iron, cobalt, erbium, nickel, europium, technetium, indium, samarium, dysprosium, ruthenium, ytterbium, yttrium, and holmium ions, and combinations thereof.

20. A method of claim 3 wherein said synthetic polymer is non-crosslinked.

21. A method of claim 3 wherein said contrast enhancing metal ion is selected from the group consisting of paramagnetic metal ions and heavy metal ions.

22. A method of claim 21 wherein said contrast enhancing metal ion is a paramagnetic metal ion selected from the group consisting of gadolinium, manganese, copper, chromium, iron, cobalt, erbium, nickel, europium, technetium, indium, samarium, dysprosium, ruthenium, ytterbium, yttrium, and holmium ions, and combinations thereof.

23. A method of claim 2 wherein said methoxylated polymer is non-crosslinked.

24. A method of claim 2 wherein said methoxylated polymer is selected from the group consisting of arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xanthan gum, starch, carboxymethylcellulose, hydroxymethylcellulose, hydroxypropylmethylcellulose, methylcellulose, methoxycellulose, polypeptides, polyalcohols, and polysaccharides containing at least one aldose, ketose, acid or amine selected from the group consisting of erythrose, threose, ribose, arabinose, xylose, lyxose, allose, altrose, glucose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid.

25. A method of claim 24 wherein said methoxylated polymer is selected from the group consisting of pectins, pectic acids, and polysaccharides containing glucaric acid, or galacturonic acid.

26. A method of claim 2 wherein said contrast enhancing metal is selected from the group consisting of paramagnetic metal ions and heavy metal ions.

27. A method of claim 26 wherein said contrast enhancing metal is a paramagnetic metal ion selected from the group consisting of gadolinium, manganese, copper, chromium, iron, cobalt, erbium, nickel, europium, technetium, indium, samarium, dysprosium, ruthenium, ytterbium, yttrium, and holmium ions, and combinations thereof.

28. A method of claim 1 wherein said methoxylated polymer is non-crosslinked.

29. A method of claim 1 wherein said methoxylated polymer is selected from the group consisting of arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xanthan gum, starch, carboxylmethylcellulose, hydroxymethylcelluilose, hydroxypropylmethylcellulose, methylcellulose, methoxycellulose, polypeptides, polyalcohols, and polysaccharides containing at least one aldose, ketose, acid or amine selected from the group consisting of erythrose, threose, ribose, arabinose, xylose, lyxose, allose, altrose, glucose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid.

30. A method of claim 29 wherein said methoxylated polymer is selected from the group consisting of pectins, pectic acids, and polysaccharides containing glucaric acid, or galacturonic acid.

31. A method of claim 1 wherein said contrast enhancing metal is selected from the group consisting of paramagnetic metal ions and heavy metal ions.

32. A method of claim 31 wherein said contrast enhancing metal is a paramagnetic metal ion selected from the group consisting of gadolinium, manganese, copper, chromium, iron, cobalt, erbium, nickel, europium, technetium, indium, samarium, dysprosium, ruthenium, ytterbium, yttrium, and holmium ions and combinations thereof.

33. A method of providing an image of an internal region of a patient comprising (i) administering to the patient a contrast medium comprising gel particles of less than about 90$\mu$ in mean diameter, said gel particles comprising at least one unmethoxylated natural or unmethoxylated modified natural polymer entrapping at least one contrast enhancing metal; and (ii) scanning the patient using magnetic resonance imaging to obtain visible images of the region, wherein said polymer is selected from the group consisting of hyaluronic acid and alginic acid.

34. A method for diagnosing the presence of diseased tissue in a patient comprising (i) administering to the patient a contrast medium comprising gel particles of less than about 90$\mu$ in mean diameter, said gel particles comprising at least one unmethoxylated natural or unmethoxylated modified natural polymer entrapping at least one contrast enhancing metal; and (ii) scanning the patient using magnetic resonance imaging to obtain visible images of any diseased tissue in the patient, wherein said polymer is selected from the group consisting of hyaluronic acid and alginic acid.

35. A method of claim 2 wherein said methoxylated natural or methoxylated modified natural polymer is a polysaccharide.

36. A method of claim 1 wherein said methoxylated natural or methoxylated modified natural polymer is a polysaccharide.

* * * * *

UNITED STATES PATENT AND TRADEMARK OFFICE
CERTIFICATE OF CORRECTION

PATENT NO.    : 5,976,500
DATED         : November 2, 1999
INVENTOR(S)   : Evan C. Unger Page 1 of 1

It is certified that error appears in the above-identified patent and that said Letters Patent is hereby corrected as shown below:

Column 6,
Line 1, please delete "mixing., etch." and insert -- mixing, etc. -- therefor.

Column 7,
Line 17, please insert a -- . -- after "derivatives".

Column 8,
Line 5, please insert a -- . -- after "bridges".
Line 11, please insert a -- . -- after "(DTSSP)".

Column 12,
Line 49, please insert a -- . -- after "shown in Table 1".

Column 13,
Line 16, please insert a -- . -- after "(last entry)".

Column 14,
Line 65, please delete "Gel" and insert -- Gels -- therefor.

Column 15,
Line 3, please insert a -- . -- after "solutions".

Column 18,
Line 13, please delete "Table 12" and insert -- Table 13 -- therefor.

Column 21,
Line 51, please delete "hydroxymethylcelluilose" and insert
-- hydroxymethycellulose -- therefor.

Signed and Sealed this

Twenty-first Day of May, 2002

Attest:

Attesting Officer

JAMES E. ROGAN
Director of the United States Patent and Trademark Office